United States Patent [19]
Yamauchi et al.

[11] Patent Number: 5,688,390
[45] Date of Patent: Nov. 18, 1997

[54] OXYGEN CONCENTRATION SENSOR

[75] Inventors: Masanobu Yamauchi, Kariya; Isao Watanabe, Nagoya; Toshihiro Sakawa, Toyohashi, all of Japan

[73] Assignee: Nippondenso Co., Ltd., Kariya, Japan

[21] Appl. No.: 584,464

[22] Filed: Jan. 11, 1996

[30] Foreign Application Priority Data

Jan. 12, 1995 [JP] Japan .................................. 7-020937

[51] Int. Cl.⁶ .............................................. G01N 27/409
[52] U.S. Cl. ........................... 204/426; 204/424; 204/428
[58] Field of Search ............................... 204/421–429

[56] References Cited

U.S. PATENT DOCUMENTS

| | | | |
|---|---|---|---|
| 4,277,323 | 7/1981 | Muller et al. | 204/426 |
| 4,383,907 | 5/1983 | Legrand et al. | 204/426 |
| 4,980,044 | 12/1990 | Ker . | |
| 5,419,828 | 5/1995 | Nakano et al. | 204/425 |
| 5,421,984 | 6/1995 | Saito et al. | 204/424 |

FOREIGN PATENT DOCUMENTS 63-11644   4/1988   Japan .

*Primary Examiner*—T. Tung
*Attorney, Agent, or Firm*—Cushman, Darby & Cushman IP Group of Pillsbury Madison & Sutro LLP

[57] ABSTRACT

A laminated type oxygen concentration sensor includes a laminated type oxygen concentration sensor element having a plate shape with a flange on a side surface thereof, and a housing in a tubular shape having an inclination seat inclined in a central axial direction thereof. The housing supports the laminated type oxygen concentration sensor element by contacting the inclination seat with the flange of the laminated type oxygen concentration sensor element at an outer circumference of the inclination seat. Since the sensor element is supported by contacting the flange with the inclination seat of the housing at the outer circumference of the inclination seat, the pressure per unit area imposed on the sensor element is minimized and cracking of the sensor element is prevented.

9 Claims, 6 Drawing Sheets

5,688,390

OXYGEN CONCENTRATION SENSOR

CROSS REFERENCE TO RELATED APPLICATION

This application is based on and claims priority from Japanese Patent Application No. 7-20937 filed on Jan. 2, 1995, incorporated herein by reference.

BACKGROUND OF THE INVENTION
1. Field of the Invention

The present invention relates to an oxygen concentration sensor used for air/fuel ratio control of an automobile engine.

2. Description of Related Art

A conventional laminated type oxygen concentration sensor includes, for example, a tubular housing and a laminated type oxygen concentration sensor element inserted in the housing.

As shown in FIG. 9, the above-described sensor element 92 has a flange 920 supported by an inclination seat 91 mounted on a housing 90. Flange 920 has a taper portion 93 on a position facing inclination seat 91 of housing 90, and taper portion 93 has a contacting portion 931 contacting inclination seat 91 of housing 90.

Powder 13 is filled and pressurized from the top of flange 920 by a pad 14 and a supporter 15 for fixing sensor element 92 into housing 90 and for maintaining air-tightness of the inside of an oxygen concentration sensor. Thus, in the oxygen concentration sensor, the gas in a reference gas chamber is prevented from mixing with the gas in a measured gas chamber.

Since the inner circumference of taper 93 is a contacting portion 931 contacting inclination seat 91, the thinnest part of sensor element 92 will be subjected to force from inclination seat 91.

In other words, as shown in FIG. 5, principal stress F' by the force W' applying on the portion A' of the taper from the inclination seat acts on the tapered surface S'. The area of the tapered surface S' is minimized when the portion A' on the taper is the innermost circumferential part. Therefore, the principal stress acting on the unit area is maximized at this time.

The inventors have found that the above force acting on sensor element 92 may cause cracking of sensor element 92 when powder 13 is filled and pressurized when the oxygen concentration sensor shown in FIG. 7 is assembled.

A laminated type oxygen concentration sensor where a flange is formed only on the side thereof has the following particular problem, compared with a cup-shaped oxygen concentration sensor where a flange is formed on all the circumference of the sensor.

When sensor element 92 is supported by housing 90 by inclination seat 91 of the housing contacting with flange 920 of sensor element 92, the contacting surface of flange 920 with inclination seat 91 will be subjected to enormous force compared with the one of a cup-shaped sensor where a flange is formed on all the circumference thereof. Therefore, cracking of the flange may be caused.

SUMMARY OF THE INVENTION

In light of the above-described problem, the present invention provider a laminated type oxygen concentration sensor having a flange only on the side thereof, in which cracking of the flange can be prevented and air-tightness in both the reference gas chamber and the measured gas chamber can be secured.

As a result of analyzing the mechanism of how the flange cracks in detail, as shown in FIG. 7, the inventors have found cracking of the flange tends to occur and certain air-tightness cannot be obtained only when the relationship of $\alpha<\beta$ is establized ($\alpha$ is an opening angle of taper 93 and $\beta$ is an opening angle of inclination seat 91) in case housing 90 and sensor element 92 are manufactured.

According to the present invention, a laminated type oxygen concentration sensor includes a laminated type oxygen concentration sensor element in a plate shape having a flange on a side surface of the plate shape, and a housing in a tubular shape having an inclination seat inclining in a central axial direction of the tubular shape. The housing supports the laminated type oxygen concentration sensor element by contacting the inclination seat with the flange of the laminated type oxygen concentration sensor element at an outer circumference of the inclination seat.

As the sensor element is supported by contacting the flange with the inclination seat of the housing at the outer circumference of the inclination seat, the pressure per unit area imposed on the sensor element is minimized and cracking of the sensor element is prevented. Therefore, the sensor element can be securely and easily mounted in the housing without any major change of the shape of the sensor element.

Since only a certain limited portion contacts the housing, it is not necessary that the taper portion of the sensor element and the inclination seat of the housing have the same shape and that the whole surface of the flange has to contact with the whole surface of the inclination seat evenly. Therefore, the flange of the sensor element and the housing can be easily machined.

As described above, the present invention can provide an oxygen concentration sensor in which cracking of an element is prevented and the sensor element can be easily mounted in the housing with highly secured air-tightness even in a laminated type oxygen sensor having the flange formed only on the side surface thereof.

Other objects and features of the invention will appear in the course of the description thereof, which follows.

BRIEF DESCRIPTION OF THE DRAWINGS

Additional objects and advantages of the present invention will be more readily apparent from the following detailed description of preferred embodiments thereof when taken together with the accompanying drawings in which.

DETAILED DESCRIPTION OF PREFERRED EMBODIMENTS

The preferred embodiments of the present invention are described with reference to the accompanying drawings.

An oxygen concentration sensor i having a laminated type sensor element 3 according to a first embodiment is shown in FIGS. 1–4.

Figure 1:
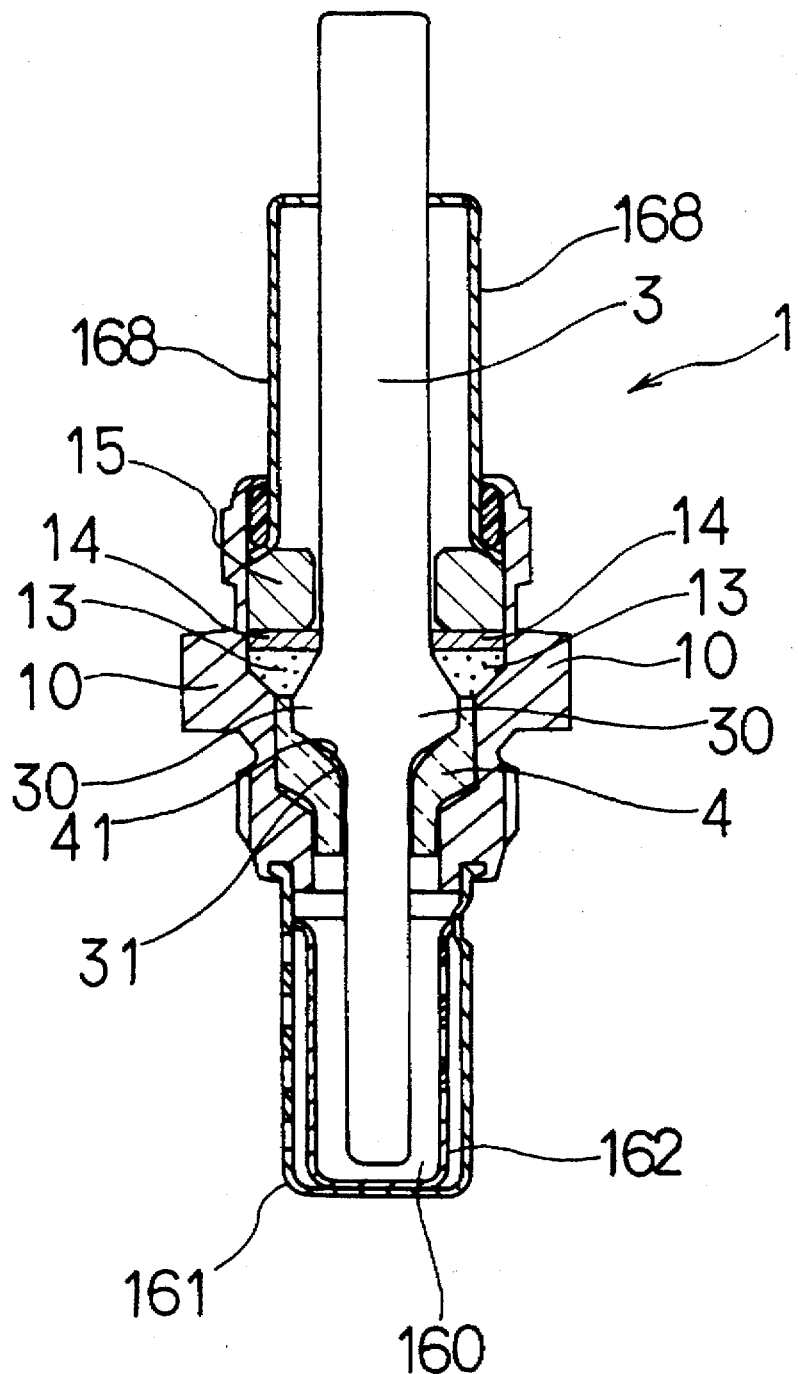
FIG. 1 is an explanatory view of the main portion of an oxygen concentration sensor having a laminated type sensor element according to a first embodiment.
Figure 2:
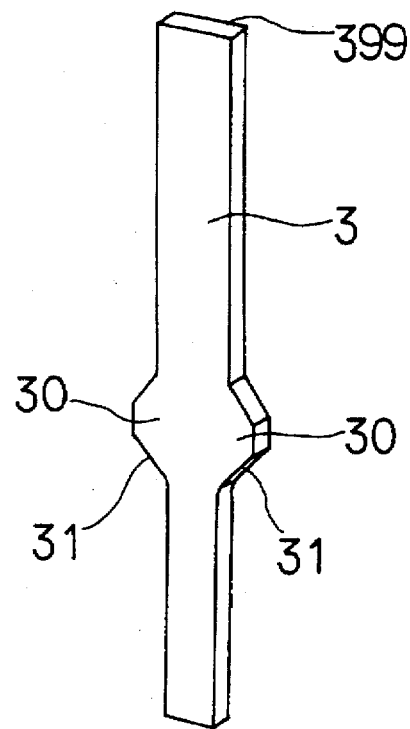
FIG. 2 is a perspective view of the laminated type sensor element according to the first embodiment.
Figure 3:
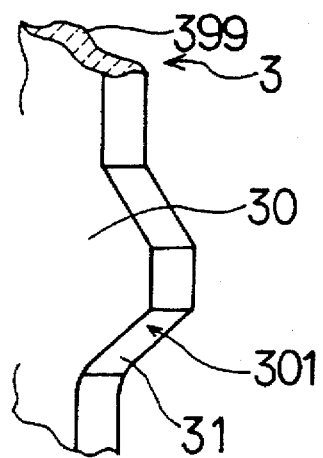
FIG. 3 is an enlarged view of the main portion of the laminated type sensor element according to the first embodiment.

As shown in FIGS. 1–3, oxygen concentration sensor 1 has a tubular housing 10 and a laminated type sensor element 3 inserted into housing 10, with an insulator 4 between housing 10 and sensor element 3. Sensor element 3 has a flat plate shape and a built-in heater.

Sensor element 3 has a flange 30 supported by an inclination seat 41 disposed on insulator 4. Flange 30 has a taper 31 at a position facing inclination seat 41 on insulator 4, and the outer circumference of taper 31 contacts with inclination seat 41 on insulator 4 with a contacting portion 301.

Figure 9:
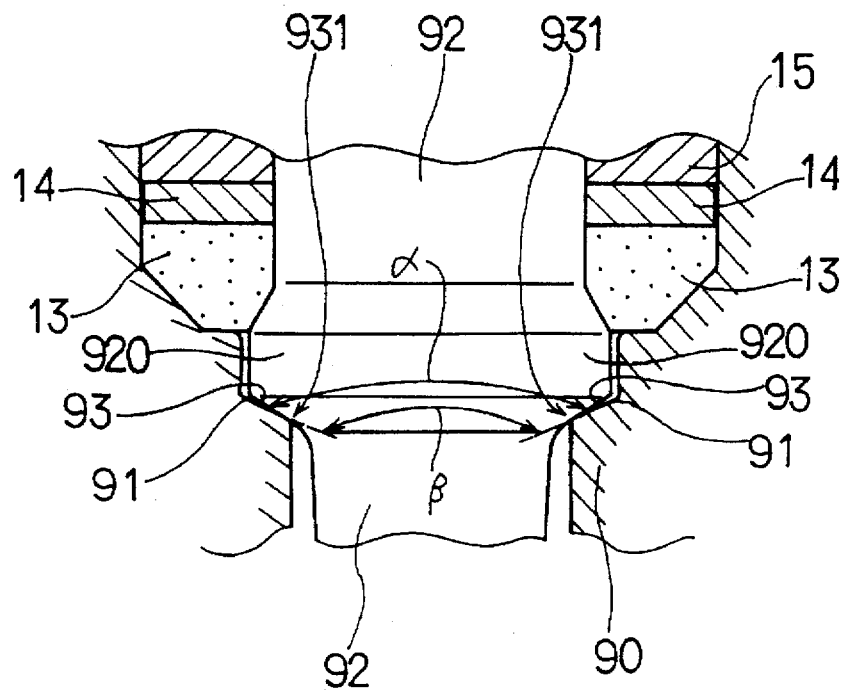
FIG. 9 is an explanatory view of a conventional type of a sensor element.

As shown in FIG. &., sensor element 3 is supported by inclination seat 41 on insulator 4 contacting only contacting portion 301. Angle γ is an opening angle of inclination seat 41 of insulator 4, angle γ being different from the opening angle β in FIG. 9 of inclination seat 91 of housing 90.

On the other hand, insulator 4 has a taper 42 supported by an inclination seat 11 disposed on housing 10. Taper 42 is located at a position facing inclination seat 11 on housing 10. The outer circumference of taper 42 has a contacting portion with inclination seat 11 on housing 10. Insulator 4 is supported by inclination seat 11 of housing 10 with a packing 52 disposed on the contacting portion.

On flange 30, powder 13 is filled and pressurized by a pad 14 and a supporter 15. Sensor element 3 are fixed in housing 10 by pressure of powder 13, pad 14 and supporter 15. A exhaust chamber 160 is formed by exhaust covers 161 and 162 disposed below housing 10. Sensor element 3 has pores 399 for introducing atmosphere in its axial direction.

Therefore, when the force W is equal to the force W', the principal stress acting on the unit area is the smallest when the contacting portion is provided at A (outermost circumferential part).

Figure 5:
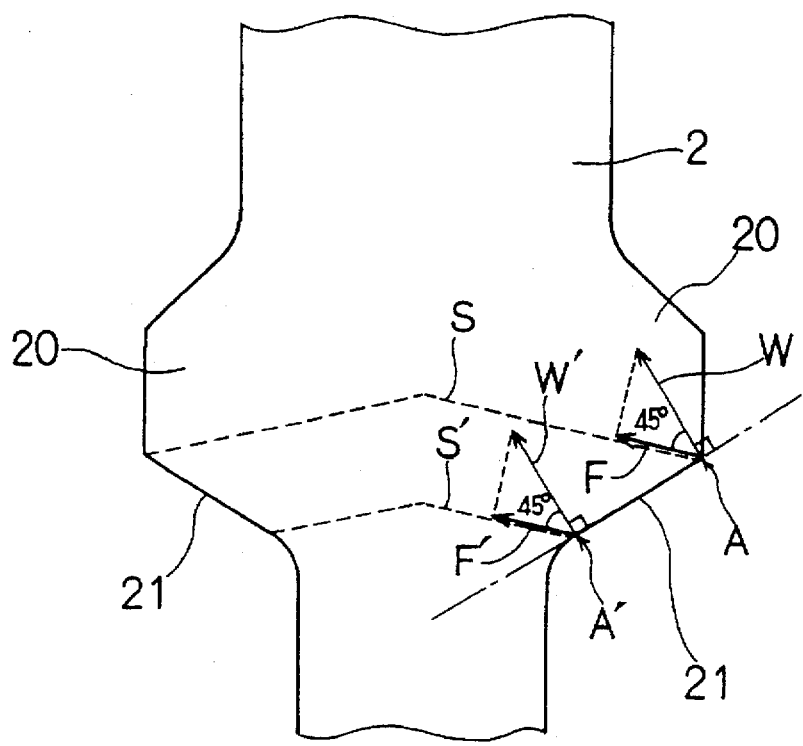
FIG. 5 is an explanatory view of function and delete according to the first embodiment.

The operation of the first embodiment is described. As shown in FIG. 5, when a force W or W' acts on a portion A or A' on taper 31 of flange 30, principal stress F or F' by the force W or W' acts on a surface S or S'. As can be seen from FIG. 5, an area of surface S is the smallest, and an area of surface S' is the largest.

Figure 4:
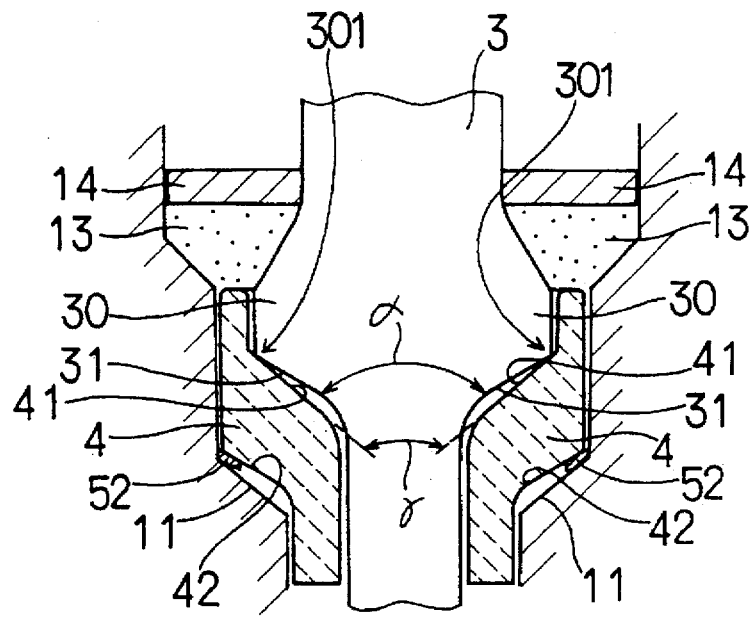
FIG. 4 is an explanatory view of the main portion of the laminated-type sensor element according to the first embodiment.

As shown in FIG. 4, in the first embodiment, the relationship of α>β is established, where α is an opening angle of taper 31 on flange 30 and β is an opening angle of taper of inclination seat 41 in housing 10. Contacting portion 301 is provided at A shown in FIG. 5.

Therefore, stress acting on sensor element 3 is minimized, and cracking of sensor element 3 is prevented even when sensor element 3 is subjected to a larger force from inclination seat 11.

Further, since the contacting portion 301 contacts only with inclination surface 41, it is not necessary to set the shape of taper 31 of sensor element 3 to be identical with the shape of inclination seat 11 of housing 10. Therefore, it is not necessary to machine taper 31 and inclination seat 11 with high accuracy.

The number of defect products due to the cracking of sensor element 3 is reduced, the yield rate is thereby improved. Further, sensor element 3 can be assembled by a larger force into housing 10, therefore, oxygen concentration sensor 1 is superior in the air tightness between sensor element 3 and housing 2.

Still further, the pressure for pressurizing powder 13 can be increased; therefore, oxygen concentration sensor 1 is superior in the air tightness in the portion where powder 13 is filled.

Comparing laminated type sensor element 3 with a cup-shaped sensor element, contacting portion 301 in laminated type sensor element 3 supported by inclination seat 11 is smaller, so that stress acting on taper 31 becomes greater.

The oxygen concentration sensor of the first embodiment can be mounted without making the size of sensor element 3 larger or causing cracking of the element.

Figure 6:
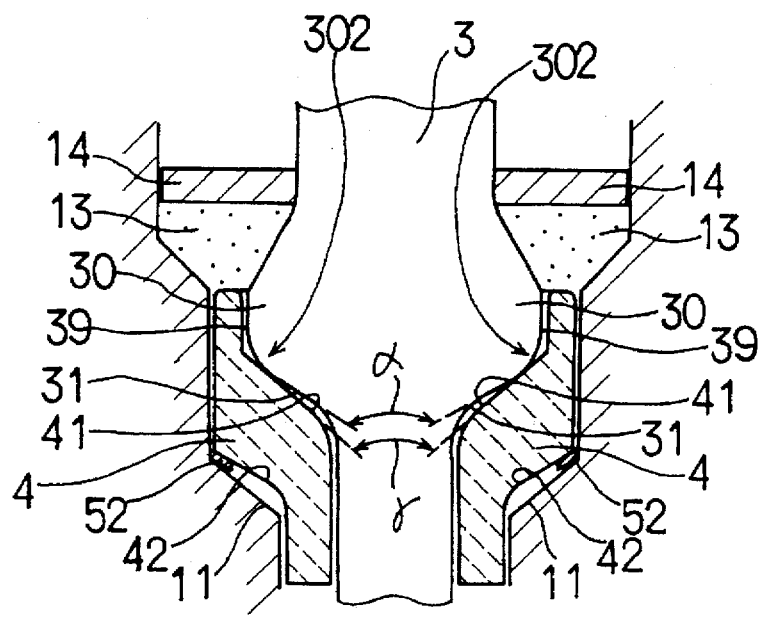
FIG. 6 is an explanatory view of the main portion of an oxygen concentration sensor having a curved contacting surface according to a second embodiment.

A second embodiment is described. As shown in FIG. 6, the second embodiment is an oxygen concentration sensor having a curved contacting portion 302 of sensor element 3.

In short, the second embodiment is similar to the oxygen concentration sensor in the above first embodiment, and has tubular housing 10 and laminated type sensor element 3 inserted into housing 10 with insulator 4 therebetween. Sensor element 3 has a contacting portion 302 contacting inclination seat 41 disposed on insulator 4, and contacting portion 302 has a curved arc-like surface. The curved surface is formed by chamfering the edge line on the border of a side surface 39 and taper 31 of flange 30. The other features are as same as in the first embodiment.

Contacting portion 302 of the oxygen concentration sensor of the second embodiment has a curved surface, which can disperse pressure acting on contacting portion 302 and reduce the stress acting on sensor element 3.

The other operations and effects are same as in the first embodiment.

Figure 7:
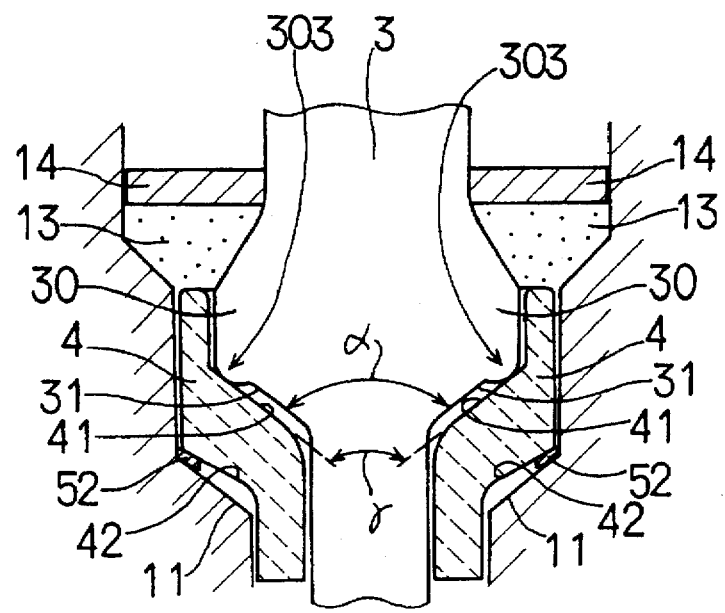
FIG. 7 is an explanatory view of the main portion of an oxygen concentration sensor having a protruding contacting portion according to a third embodiment.

Next, a third embodiment of the present invention is described. As shown in FIG. 7, in an oxygen concentration sensor of the third embodiment, a contacting portion 303 of sensor element 3 protrudes toward the inclination seat 41.

In short, the third embodiment is similar to the oxygen concentration sensor in the first embodiment, and has tubular housing 10 and laminated type sensor element 3 inserted into housing 10 with insulator 4 therebetween. Sensor element 3 has a contacting portion 303 contacting inclination seat 41 disposed on insulator 4, and contacting portion 303 forms a portion protruding toward inclination seat 41. The protruding portion is formed on the entire surface of contacting portion 303.

The other features are the same as in the first embodiment.

The outer circumference of taper 31 of sensor element 3 in the oxygen concentration sensor can surely sustain the pressure.

The ether operations and effects are same as in the first embodiment.

Figure 8:
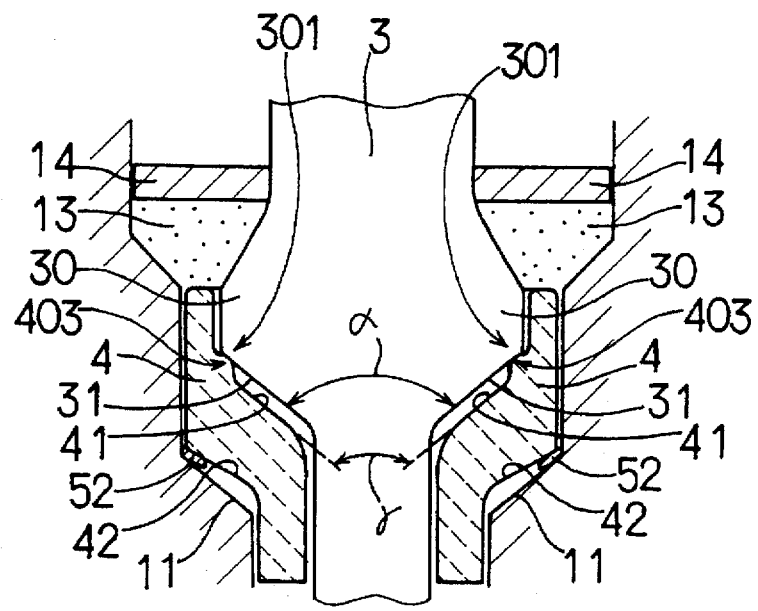
FIG. 8 is an explanatory view of the main portion of an oxygen concentration sensor having a protruding tilting seat according to a fourth embodiment.

Next, a fourth embodiment is described. In an oxygen concentration sensor of the fourth embodiment, a contacting portion of insulator 4 forms a protruding portion 403 as shown in FIG. 8.

In short, the present embodiment is similar to the oxygen concentration sensor in the first embodiment, and has tubular housing 10 and laminated type sensor element 3 inserted into housing 10 with insulator 4 therebetween. Sensor element 3 has a contacting portion 301 contacting with inclination seat 41 disposed on insulator 4. A protruding portion 403 protruding toward the contacting portion 301 is formed on inclination seat 41 of insulator 4. The protruding portion 403 completely supports the entire surface of contacting portion 301.

The other features are same as in the first embodiment.

In the fourth embodiment, the oxygen concentration sensor according to the present invention can be structured by changing the shape of only insulator 4, which can be easily designed for the complicated shape. The ocher operations and effects are the same as in the first embodiment.

Figure 10:
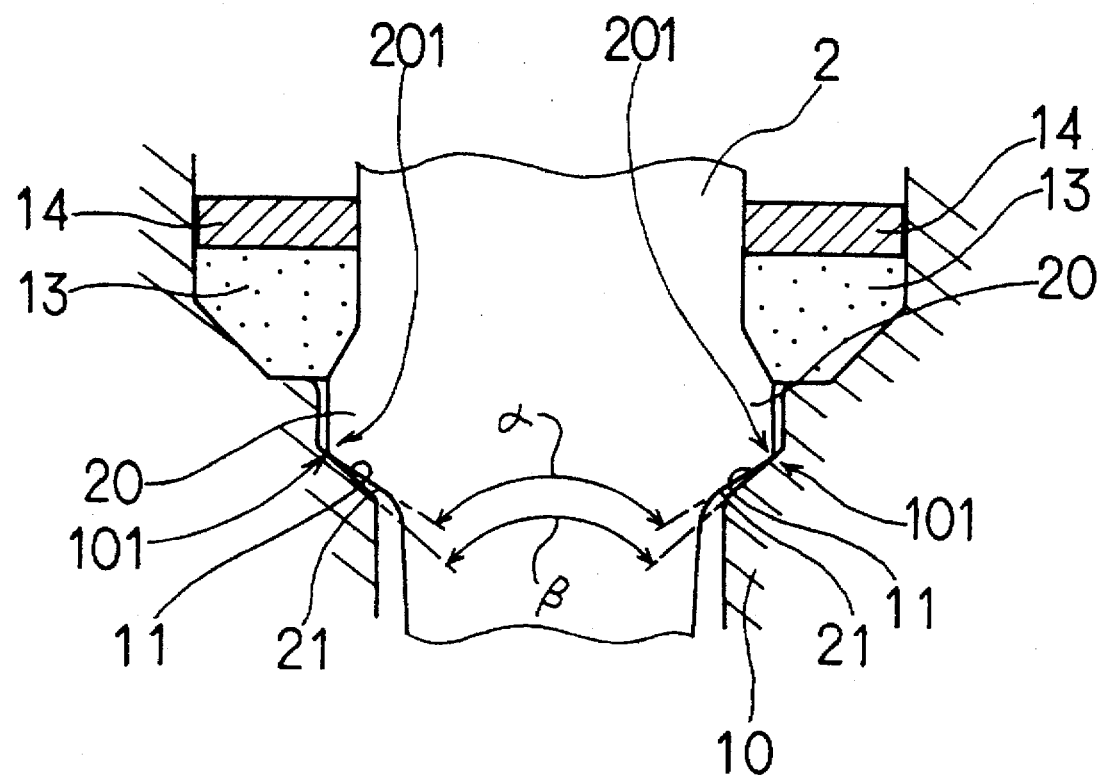
FIG. 10 is an explanatory view of a modification of the fourth embodiment.

Further, in the above embodiments shown in FIG. 4, 6, 7 and 8, insulator 4 is disposed between flange 30 of sensor element 3 end housing 10; however, as shown in FIG. 10, the same effect can be obtained even when flange 201 directly contacts with housing 10.

According to the above embodiments, the flange of the sensor element is formed on the surface having a narrower width, however, it is not limited that the flange is formed on the side of the sensor element according to the present invention. For instance, the flange can be formed on a wider width surface of the sensor element. Furthermore, the flange can be formed on the entire surface of the sensor element.

That is, the present invention can be applied to any kind of laminated type oxygen concentration sensor element where a flange cannot be formed on the whole circumference like a cup-shaped oxygen concentration sensor element.

Although the present invention has been fully described in connection with the preferred embodiments thereof with reference to the accompanying drawings, it is to be noted that various changes and modifications will become apparent to those skilled in the art. Such changes and modifications are to be understood as being included within the scope of the present invention as defined by the appended claims.

What is claimed is:

1. A laminated oxygen concentration sensor comprising:
   a laminated oxygen concentration sensor element having a plate shape with a flange on a side surface of said plate shape, said flange including a taper surface; and
   a housing in a tubular shape having an inclination seat inclining in a central axial direction of said tubular shape, said housing supporting said laminated oxygen concentration sensor element by contacting said inclination seat with said taper surface of said flange at a circumference of said inclination seat;
   wherein an opening angle of said taper surface is greater than an opening angle of said inclination seat.

2. A laminated oxygen concentration sensor according to claim 1, wherein said laminated oxygen concentration sensor element is supported by said inclination seat of said housing with a packing therebetween.

3. A laminated oxygen concentration sensor according to claim 1, wherein said flange has a protruding portion which protrudes toward said inclination seat.

4. A laminated oxygen concentration sensor comprising:
   a laminated oxygen concentration sensor element having a plate shape with a flange on a side surface of said plate shape; and
   a housing in a tubular shape having an inclination seat inclining in a central axial direction of said tubular shape, said housing supporting said laminated oxygen concentration sensor element by contacting said inclination seat with said flange at only an outer circumference of said inclination seat.

5. A laminated oxygen concentration sensor according to claim 4, wherein said flange has a curved surface.

6. A laminated oxygen concentration sensor comprising:
   a laminated oxygen concentration sensor element having a plate shape with a flange on a side surface of said plate shape, said flange including a taper surface; and
   a housing in a tubular shape having an inclination seat inclining in a central axial direction of said tubular shape; and
   an insulator disposed between said flange and said inclination seat, said insulator having an inclination seat contacting said flange at only an outer circumference of said inclination seat of said insulator.

7. A laminated oxygen concentration sensor according to claim 6, wherein an opening angle of said taper surface is greater than an opening angle of said inclination seat of said insulator.

8. A laminated oxygen concentration sensor comprising:
   a laminated oxygen concentration sensor element having a plate shape with a flange on a side surface of said plate shape, said flange including a taper surface; and
   a housing in a tubular shape having an inclination seat inclining in a central axial direction of said tubular shape; and
   an insulator disposed between said flange and said inclination seat, said insulator including a protruding portion contacting said flange at an outer circumference of said inclination seat of said insulator.

9. A laminated oxygen concentration sensor according to claim 8, wherein an opening angle of said taper surface is greater than an opening angle of said inclination seat of said insulator.

* * * * *